(12) United States Patent
Suzuki et al.

(10) Patent No.: US 10,568,607 B2
(45) Date of Patent: Feb. 25, 2020

(54) DEVICE, METHOD OF MANUFACTURING THE DEVICE, AND METHOD OF MANUFACTURING ARRAY TYPE OF ULTRASOUND PROBE

(71) Applicants: ULVAC, INC., Kanagawa (JP); TOHOKU UNIVERSITY, Miyagi (JP)

(72) Inventors: Taichi Suzuki, Kanagawa (JP); Koh Fuwa, Kanagawa (JP); Ken Maehira, Kanagawa (JP); Yasutomo Ohashi, Kanagawa (JP); Katsuhiro Fujita, Kanagawa (JP); Yoichi Haga, Miyagi (JP); Tadao Matsunaga, Miyagi (JP)

(73) Assignees: ULVAC, INC., Kanagawa (JP); TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 16/316,699

(22) PCT Filed: Aug. 15, 2017

(86) PCT No.: PCT/JP2017/029364
§ 371 (c)(1),
(2) Date: Jan. 10, 2019

(87) PCT Pub. No.: WO2018/047585
PCT Pub. Date: Mar. 15, 2018

(65) Prior Publication Data
US 2019/0290244 A1    Sep. 26, 2019

(30) Foreign Application Priority Data

Sep. 7, 2016   (JP) ................................ 2016-175076

(51) Int. Cl.
*A61B 8/00*    (2006.01)
*A61B 8/08*    (2006.01)
(Continued)

(52) U.S. Cl.
CPC .......... *A61B 8/4494* (2013.01); *A61B 8/0891* (2013.01); *A61B 8/14* (2013.01);
(Continued)

(58) Field of Classification Search
CPC ...... H04R 17/00; H04R 31/00; A61B 8/0891; A61B 8/14; A61B 8/4236; A61B 8/4416; A61B 8/4494
(Continued)

(56) References Cited

U.S. PATENT DOCUMENTS 4,628,223 A    12/1986  Takeuchi et al.
4,658,176 A     4/1987  Nakaya et al.
(Continued)

FOREIGN PATENT DOCUMENTS

JP    60-86999 A    5/1985
JP    61-53562 A    3/1986
(Continued)

OTHER PUBLICATIONS

International Search Report and Written Opinion for PCT Patent App. No. PCT/JP2017/029364 dated (Sep. 19, 2017) with English transltaiton of the ISR.
(Continued)

*Primary Examiner* — J. San Martin
(74) *Attorney, Agent, or Firm* — Cermak Nakajima & McGowan LLP; Tomoko Nakajima

(57) ABSTRACT

A ultrasound probe according to this invention is provided with: a first dry film resist having a plurality of first apertures formed in an array shape, and respectively supporting the piezoelectric elements in close contact with a rim part of each of the first apertures in a state of partly exposing the function elements; a second dry film resist laminated on the first dry film resist, and also having second apertures respectively enclosing each of the function elements, the second
(Continued)

dry film resist being of a thickness equivalent to that of each of the function elements; and a third dry film resist laminated on the second dry film resist, and also having third apertures, and respectively sandwiching each of the piezoelectric elements with the first dry film resist in a state of partly exposing the piezoelectric elements in close contact with a rim part of each of the third apertures.

4 Claims, 4 Drawing Sheets

(51) Int. Cl.
*H04R 17/00* (2006.01)
*H04R 31/00* (2006.01)
*A61B 8/14* (2006.01)

(52) U.S. Cl.
CPC .......... *A61B 8/4416* (2013.01); *H04R 17/00* (2013.01); *H04R 31/00* (2013.01)

(58) Field of Classification Search
USPC ................ 29/292.1, 294, 609.1; 310/334
See application file for complete search history.

(56) References Cited

U.S. PATENT DOCUMENTS

| | | | |
|---|---|---|---|
| 2008/0076974 A1* | 3/2008 | Yamazaki | A61B 5/0002 600/300 |
| 2008/0116765 A1 | 5/2008 | Sugiura et al. | |
| 2016/0035963 A1* | 2/2016 | Kurokawa | A61B 8/4483 367/7 |

FOREIGN PATENT DOCUMENTS

| | | |
|---|---|---|
| JP | 5-292598 A | 11/1993 |
| JP | 2006-051105 A | 2/2006 |
| JP | 2006-094459 A | 4/2006 |

OTHER PUBLICATIONS

International Preliminary Report on Patentability for PCT Patent App. No. PCT/JP2017/029364 dated (Mar. 21, 2019).

* cited by examiner

DEVICE, METHOD OF MANUFACTURING THE DEVICE, AND METHOD OF MANUFACTURING ARRAY TYPE OF ULTRASOUND PROBE

This application is a national phase entry under 35 U.S.C. § 371 of PCT Patent Application No. PCT/JP2017/029364, filed on Aug. 15, 2017, which claims priority under 35 U.S.C. § 119 to Japanese Patent Application No. 2016-175076, filed Sep. 7, 2016, both of which are incorporated by reference.

TECHNICAL FIELD

The present invention relates to a device and a method of manufacturing the device and, in particular, to an ultrasound probe as a device for measuring, by using a pulse-echo method, a diameter of blood vessel of a living body, in more detail, of a wrist radius artery, and also relates to an ultrasound probe as the device and a method of manufacturing the same.

BACKGROUND ART

Recently, in moving into the aging society, there have been developed various kinds of appliances which can be easily handled by a user and in which such information relating to the living body as is required for healthcare can be easily obtained. As an example of this kind of appliances, there is known an ultrasound probe for measuring, by using a pulse-echo method, the diameter of blood vessel of a wrist radius artery. As the ultrasound probe, the mainstream is a wearable and flexible array type in which a plurality of piezoelectric elements as function elements for transmitting/receiving ultrasound are disposed in an array shape (see, for example, Patent Document 1). By disposing a plurality of piezoelectric elements in the array shape in this manner, without the necessity of relying on specialists such as clinical doctors, clinical engineers, and the like, the user may attach the product thus obtained to the skin on the wrist radius artery so that the expansion and contraction of the artery radius can be measured by the ultrasound and converted into blood pressure. In addition, by measuring the pulsation of the blood vessels, without being limited to the measuring of the blood pressure, not only the measurements of the brain waves and heart rates, but also the evaluation of hardness of the blood vessels can be evaluated from the change with time of the expansion and contraction of the blood vessels. As a result, it becomes possible to routinely monitor the diseases of the blood vessels such as arterial sclerosis and cardiac disease. It is expected, out of the correlation with the vascular endothelial disorders, to apply the measurements to the prevention and care of hypertension and diabetes.

In the above-mentioned conventional examples, grooves are formed on a block-shaped piezoelectric composite having a predetermined thickness by using a dicing machine; an electrically insulating resin is filled into the grooves thus formed; and thereafter both main surfaces in the thickness-wise direction are respectively polished by a polishing apparatus. Then, on both the main surfaces of the piezoelectric composite, divided electrodes and overall electrodes are respectively formed by a sputtering method or a plating method. In this manner, there is manufactured a product in which each of the piezoelectric elements to transmit/receive ultrasound is arranged in an array shape at a certain interval.

It is known that the piezoelectric ceramics such as PZT and barium titanate, and piezoelectric composite constituted by piezoelectric single crystal such as PMN-PT and the like will have the oscillatory frequency determined depending on their thicknesses. In this case, for example, in case PMM-PT is used as the piezoelectric element for an ultrasound probe which transmits/receives ultrasound, the characteristics will be impaired even by the change in thickness by several μm. Therefore, in a manufacturing method such as of the above-mentioned prior art in which, in order to divide into respective piezoelectric elements, resin is filled and the main surface is polished, it will be difficult to make the thickness of each of the piezoelectric elements to coincide with one another. Still furthermore, there will arise a problem in that the transmitting frequency of each of the piezoelectric elements cannot be made uniform. In this case, only those piezoelectric elements which have different transmitting frequencies can neither be replaced out of each of the piezoelectric elements arranged in an array shape. It is therefore an urgent problem to develop a structure of a device and the method of manufacturing the device, with a good yield rate, in which a plurality of function elements having a uniform thickness are disposed in an array shape at predetermined intervals.

PRIOR ART DOCUMENTS

Patent Documents

Patent Document 1: JP-2006-51105 A

SUMMARY OF THE INVENTION

Problems that the Invention is to Solve

In view of the above-mentioned points, this invention has a problem of providing a device with a structure, a method of manufacturing the device, as well as a method of manufacturing an array type of ultrasound probe, in which a plurality of function elements having a uniform thickness are disposed in an array shape at predetermined intervals.

Means for Solving the Problems

In order to solve the above problems, the device according to this invention having a plurality of function elements of predetermined thicknesses has the features comprising: a first dry film resist having a plurality of first apertures formed in an array shape, and respectively supporting the function elements in close contact with a rim part of each of the first apertures in a state of partly exposing the function elements; a second dry film resist laminated on the first dry film resist, and also having second apertures respectively enclosing each of the function elements, the second dry film resist being of a thickness equivalent to that of each of the function elements; and a third dry film resist laminated on the second dry film resist, and also having third apertures, and respectively sandwiching each of the function elements with the first dry film resist in a state of partly exposing the function elements in close contact with a rim part of each of the third apertures.

In this invention, the function elements include, aside from piezoelectric elements which are constituted by piezoelectric ceramics such as PZT, barium titanate, and a piezoelectric monocrystal such as PMN-PT, function parts necessary for performing the function of devices such as micro lenses, etc. are also included. Then, in case that the function elements are constituted as piezoelectric elements and that the device is constituted as array type of ultrasound probe for measuring, by using a pulse-echo method, a diameter of blood vessel of a living body, there may be employed an arrangement further comprising: an overall electrode formed between the first dry film resist and one main surface of each of the respective piezoelectric elements; a partial electrode respectively formed on another main surface of each of the piezoelectric elements; and a backing material covering the partial electrode. Further, in the case of having thickness equivalent to that of the function elements, the thickness of the part sandwiched by the first and third dry films may be equivalent, the thicknesses of the other parts need not be equivalent.

Further, in order to solve the above-mentioned problems, a method of manufacturing the device, which has a plurality of function elements of predetermined thicknesses, according to this invention has the features comprising the steps of: adhering, on one surface of a support member, a first dry film resist through a release sheet, and exposing and developing the first dry film resist, thereby forming a plurality of first apertures in an array shape; adhering, on a surface of the first dry film resist, a second dry film resist having a thickness equivalent to those of the function elements, and exposing and developing the second dry film resist, thereby forming, right above each of the first apertures, respective second apertures larger than the first apertures; disposing the function elements on an inside of the second apertures so as to be supported by rim parts of the first apertures; adhering, in a state of being heated, a third dry film resist on a surface of the second dry film resist, and exposing and developing the third dry film resist, thereby forming third apertures respectively so that the function elements are sandwiched together with the first dry resist film; and forming a carrier member on a surface of the third dry film resist, and releasing along an interface between the first dry film resist and the release sheet.

Still furthermore, in order to solve the above-mentioned problems, a method of manufacturing an array type of ultrasound probe for measuring, by using a pulse-echo method, a diameter of blood vessel of a living body, has the features in that it comprises the steps of: preparing a plurality of piezoelectric elements having equivalent thicknesses, and forming a first electrode film over an entire one main surface of each piezoelectric elements; adhering, through a release sheet, a first dry film resist on one surface of a support, and exposing and developing the first dry film resist, thereby forming a plurality of first apertures in an array shape; forming a second electrode film on the surface of the first dry film resist by patterning; adhering, on the surface of the first dry film resist on which the second electrode film has been formed, a second dry film resist having thicknesses equivalent to those of the piezoelectric elements, and exposing and developing the second dry film resist, thereby forming second apertures larger than the first apertures right above each of the first apertures; disposing, on an inside of the second apertures, piezoelectric elements from the main surface side on which the first electrode film has been formed, so as to be supported by rim parts of the first apertures to thereby make an overall electrode in which the first electrode film and the second electrode film are connected to each other; adhering, in a state of being heated, a third dry film resist on a surface of the second dry film resist inclusive of another main surface of the piezoelectric elements, and exposing and developing the third dry film resist, thereby forming third apertures so as to sandwich the piezoelectric elements together with the first apertures; forming partial electrodes respectively on another main surface; and forming a backing material serving as a carrier member to cover the third dry film resist and the partial electrodes, and releasing along an interface between the first dry film resist and the release sheet.

According to the above, when description is made of an example in which the device is defined to be an array type of ultrasound probe, unlike the above-mentioned prior art in which the piezoelectric elements as the function elements are subjected to polishing in the course of manufacturing the device, a plurality of piezoelectric elements that have already been polished in advance from a block-shaped article to predetermined thicknesses, i.e., having uniform oscillating frequencies, are prepared. Each of the piezoelectric elements is then placed in position into each of the first apertures that have been formed by exposing and developing the first dry film resist. It is therefore possible to make the piezoelectric elements facing the first apertures into an arrangement in which the piezoelectric elements are disposed in an array shape at a predetermined interval. Then, when at least the third dry film resist is adhered to the surface of the second dry film resist, by heating those laminated matters together, even if minute clearances were to be present between, e.g., the second apertures and the piezoelectric elements, each of the dry film resists gets partly melted to thereby fill those clearances. As a consequence, the piezoelectric elements are firmly held by each of the first through third dry film resists, whereby each of the piezoelectric elements can surely be electrically insulated. In addition, since an arrangement has been employed in which the function elements are held by each of the first through third dry film resists, the flexibility as a device will neither be impaired. In this manner, according to this invention, a plurality of function elements disposed in an array shape at a predetermined distance, can be manufactured with a good yield of products.

MODES FOR CARRYING OUT THE INVENTION

With reference to the drawings, a description will now be made of a device and a method of manufacturing the device according to an embodiment of this invention, the description being made by referring to an example in which function elements are constituted as piezoelectric elements and in which a device is constituted as an array type of ultrasound probe for measuring, by using a pulse-echo method, the diameter of blood vessel of a living body. In the following description, the terms referring to the direction such as "up or upper," "down or lower" and the like shall be understood to refer, as a basis, to the mounted posture of the ultrasound probe relative to the object to be measured as shown in FIG. 1.

Figure 1:
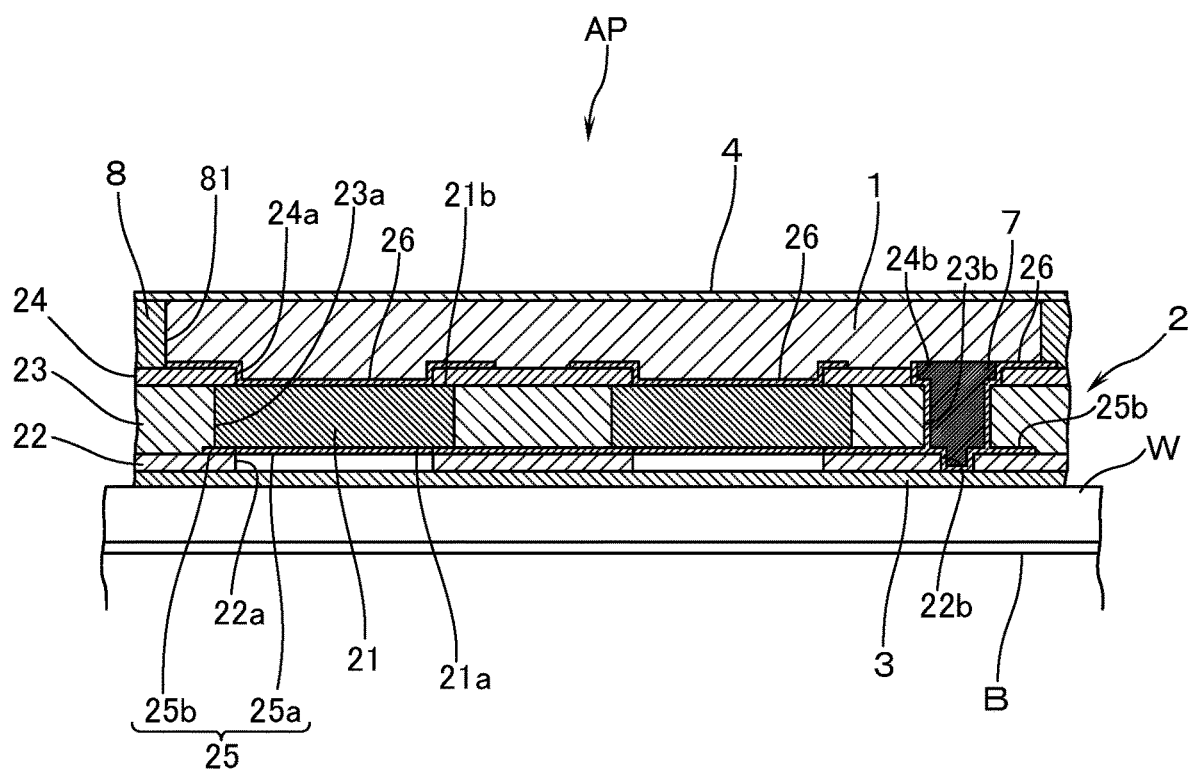
FIG. 1 is a sectional view, partly cut away, to explain an arrangement of an array type of ultrasound probe according to an embodiment of this invention.

With reference to FIG. 1, reference characters AP denote an array type of ultrasound probe, as an embodiment of this invention, for measuring the diameter of a blood vessel B of a wrist radius artery, as an object for measurement, by mounting the probe on a predetermined position of the wrist W. The ultrasound probe AP is provided with: a backing material 1; an ultrasound transmitter/receiver 2; and an acoustic matching part 3. The ultrasound probe AP is connected from a backing material 1 side to a flexible wiring substrate 4 which is constituted by polyimide and the like and which has on its surface metal wiring in a predetermined pattern.

The ultrasound transmitter/receiver part 2 is constituted by: a plurality of piezoelectric elements 21 serving as function elements which are applied with pulse voltage, and transmit ultrasound toward the blood vessel B, and receive reflected waves to be reflected after collision with the blood vessel B; a first dry film resist 22 which has a plurality of first apertures 22a formed in an array shape, and which comes into close contact with a rim part of each of the first apertures 22a in order to respectively support the piezoelectric elements 21 in a state of partly exposing thereof; a second dry film resist 23 having a thickness equivalent to that of the piezoelectric element 21, and which is laminated on the first dry film resist 22 and which has second apertures 23a to respectively enclose each of the piezoelectric elements 21; and a third dry film resist 24 which is laminated on the second dry film resist 23 and also has third apertures 24a, and sandwich each of the piezoelectric elements 21 with the first dry film resist 22 in a state of partly exposing the piezoelectric elements 21 in close contact with a rim part of each of the third apertures 24a. Between the first dry film resist 22 and one main surface 21a of each of the piezoelectric elements 21 (lower surface of the piezoelectric element 21), an overall electrode 25 is formed, and on another main surface 21b of each of the piezoelectric elements 21 (upper surface of the piezoelectric element 21), partial electrodes 26 are, respectively, formed over the entire surface.

The backing material 1 has a function of efficiently irradiating the ultrasound from each of the piezoelectric elements 21 toward the blood vessel B, as well as a function of a carrier to carry the device provided with a backing material 1, the ultrasound transmitter/receiver 2, and the acoustic matching part 3, and is constituted by a mixture of metallic powder and epoxy resin, and the like. In this case, the backing material 1 is formed on the third dry film resist 24, inclusive of the partial electrodes 26, in a manner to enclose the region in which each of the piezoelectric elements 21 is disposed in an array shape, and the thickness is set to fall within a range of 100 μm to 300 μm. Each of the piezoelectric elements 21 is constituted by a piezoelectric ceramics such as PZT, barium titanate, and by a piezoelectric single crystal such as PMN-PT. Each of the piezoelectric elements 21 is fabricated into a rectangular parallelepiped having both main surfaces 21a, 21b of 0.5 mm² in area and having 80 μm to 120 μm in predetermined thickness (preferably 90 μm). The acoustic matching part 3 is constituted by a raw material, such as polyvinyliden fluoride and the like, having an appropriate acoustic impedance on the surface of ultrasound transmitter surface. It is fabricated into a plate shape. The thickness thereof is set within a range of 10 μm to 50 μm. In adhering the acoustic matching part 3, there is a method available of using an adhesive agent, a method of adhering by using a solvent, and a method of forming by applying a vapor deposition polymerization. In case the vapor deposition polymerization is used, the resin to be used may include polyimide, parylene, polyuria and the like.

The first through third dry film resists 22, 23, 24 are constituted by the same embodiments with only difference in thicknesses. As each of these first through third dry film resists 22, 23, 24 use may be made of ones having the functions, e.g., of photo-setting, hot-melting properties, etc. There may be used conventional one in which photosensitive resin composition is applied to the surface of the sheet-shaped support made of resin (for example, TOKT-MMF-S20 series (made by Tokyo Ouka Kougyo)). In this case, as the first and third dry film resists 22, 24, selection is made of a predetermined thicknesses within a range of 20 μm to 45 μm. Then, with respect to each of the first through third dry film resists 22, 23, 24, photomasks (not illustrated) are respectively disposed to thereby expose each of the first through third dry film resists 22, 23, 24. Then, after having removed the photomasks, development is performed. At this time, in case each of the first through third dry film resists 22, 23, 24 is of negative type, non-exposed portions are removed. In this manner, each of the first through third apertures 22a, 23a, 24a having the identical opening area that has been set in advance is patterned in an array shape. Each of the first through third apertures 22a, 23a, 24a is formed so as to have a rectangular profile, but may be appropriately changed depending on the profiles of the main surfaces 21a, 21b, e.g., of the piezoelectric element 21.

In the above-mentioned ultrasound probe AP, although not particularly illustrated and described, a predetermined pulse voltage is selectively applied to each of the piezoelectric elements 21 from a conventional pulse power source through flexible wiring substrate 4. In this case, when pulse voltage in the range of 40 to 100 V is applied, ultrasound of about 20 MHz will be oscillated and, the piezoelectric element 21 will be oscillated by the ultrasound reflected at the blood vessel B. The reflected waves are measured by conversion of the oscillations into electrical signals. By the way, as to the method of measuring the diameter of the blood vessel by using ultrasound probes AP, conventional art may be utilized. Therefore, further detailed explanations thereof are omitted. Description will now be made of a method of manufacturing the above-mentioned ultrasound probes with reference to FIG. 2 and FIG. 3.

First, a plurality of piezoelectric elements 21 of the above-mentioned thickness (i.e., with a uniform oscillating frequency) are prepared, and a first electrode film 25a is formed on an entire surface of one main surface 21a of each of the piezoelectric elements 21 (see what has been shown by imaginary lines in FIG. 2(d)). Together with the above, there is prepared a support member 5 which has a rigidity such as silicon and the like and which has been applied over an entire upper surface thereof with a heat-peelable release sheet 6. By the way, as the release sheet 6, there may be used conventional ones, and there may also be used a UV-curable release sheet. Once the support member 5 has been prepared, a first dry film resist 22 is adhered on the release sheet 6. In this case, in order to adhere the first dry film resist 22 with good adhesive properties over the entire surface of the release sheet 6, use may be made of a roll-type of laminating apparatus in which pressure bonding is made with rolls while heating, or of a vacuum type of laminating apparatus in which pressure bonding is made while heating inside a vacuum chamber in reduced pressure. This invention shall, however, not be limited to the above examples.

Figure 2:
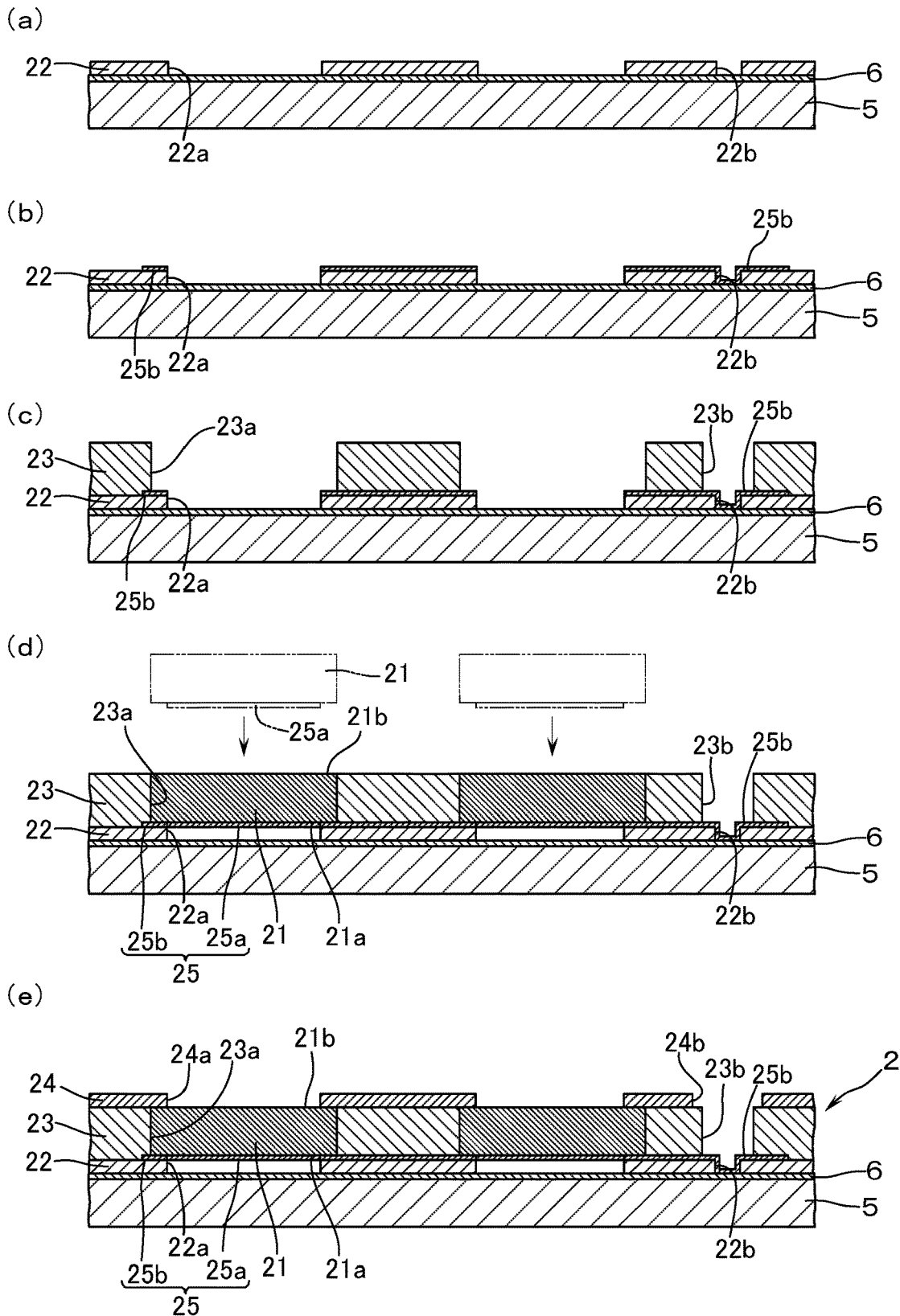
FIGS. 2 (*a*) through (*e*) are sectional views respectively showing the manufacturing steps of array type of ultrasound probe shown in FIG. 1.

Then, a photomask (not illustrated) is disposed to expose the first dry film resist 22 and, after having removed the photomask, development is performed so as to form a plurality of first apertures 22a in an array shape (see FIG. 2 (*a*)). In this embodiment, at the same time as the forming of the first apertures 22a, the first dry film resist 22 has formed therein apertures 22b for use in forming wiring layer to make wiring connection with a flexible wiring substrate 4. By the way, since exposure, development, removal of exposed portion or non-exposed portion may utilize the conventional art, detailed explanations thereof are omitted here. After having formed the first apertures 22a and the apertures 22b for forming wiring layer, a second electrode film 25b is formed on the first dry film resist 22 by patterning (see FIG. 2(*b*)). As the first and the second electrode films 25a, 25b, conductive metallic materials such as gold, copper, chromium and the like are used. For the formation of the electrode films 25a, 25b, sputtering apparatus, vacuum evaporation (deposition) apparatus, and the like are used.

Next, on top of the first dry film resist 22 on which the second electrode film 25b has been formed, a second dry film resist 23 having the thickness equivalent to that of the piezoelectric element 21 is adhered in a manner similar to the above, thereby respectively forming, by exposure and development, second apertures 23a which are larger than the first apertures 22a, right above each of the first apertures 22a (see FIG. 2 (*c*)). In this case, the second apertures 23a are set so as to become slightly larger than the profile of the piezoelectric elements 21. Further, also right above the apertures 22b for forming the wiring layer 22b, apertures 23b for forming other wiring layers are formed. Then, in order to be supported by the rim part of the first apertures 22a, the piezoelectric elements 21 are respectively disposed onto the inside of the second apertures 23a from the side of the main surface 21a on which the first electrode film 25a has been formed. According to this arrangement, an overall electrode 25 is formed in which the first electrode film 25a and the second electrode film 25b are connected together (see FIG. 2(*d*)). Once each of the piezoelectric elements 21 has been placed in position, in a manner similar to the above, a third dry film resist 24 is adhered on the second dry film resist 23 inclusive of another main surface 21b of the piezoelectric element 21. Third apertures 24a are thus formed by exposure and development so that the piezoelectric elements 21 can be sandwiched together with the first apertures 22a and the third apertures 24a (see FIG. 2(*e*)).

Figure 3:
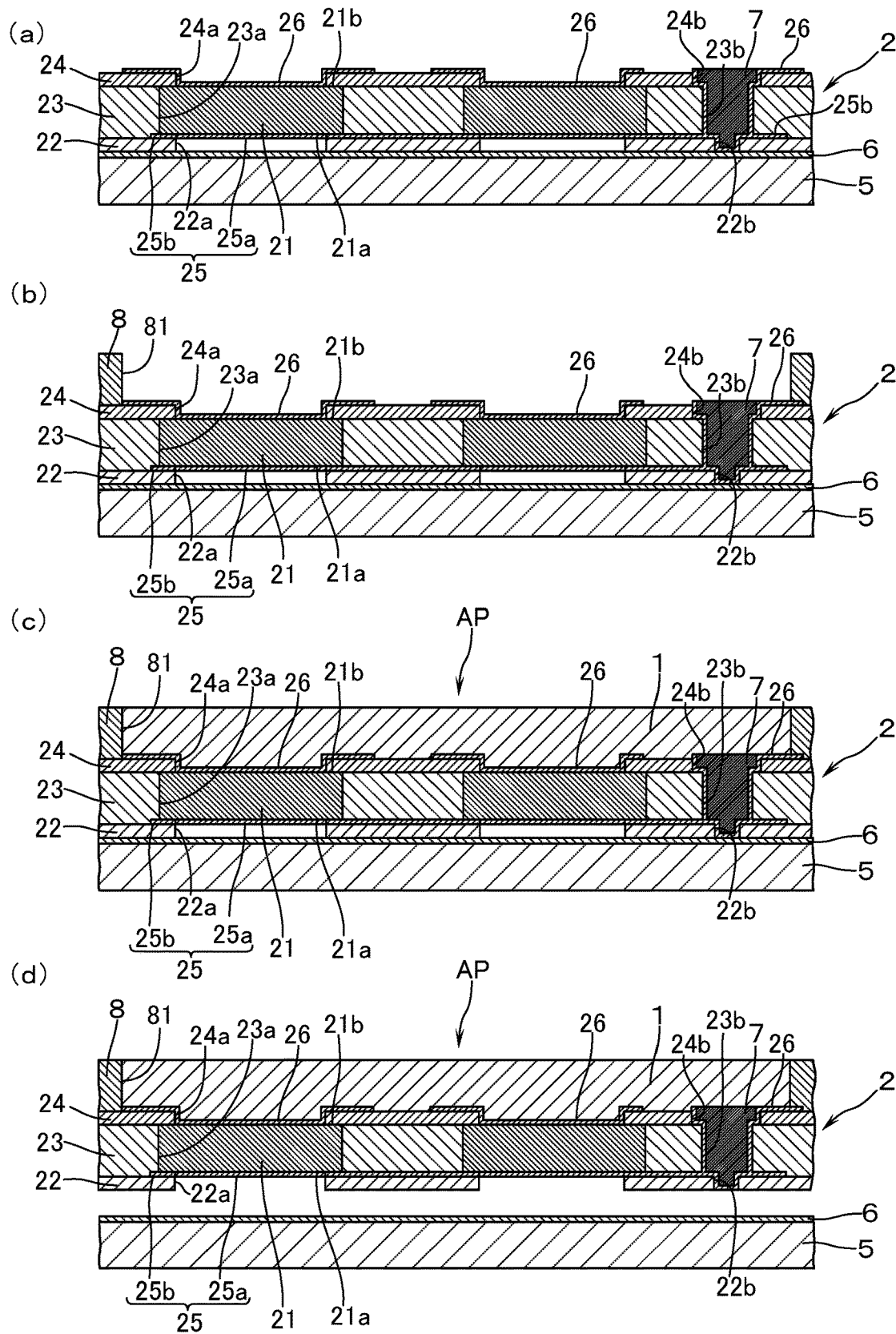
FIGS. 3 (*a*) through (*d*) are sectional views respectively showing the manufacturing steps of array type of ultrasound probe shown in FIG. 1.

Next, once the third apertures 24a have been formed, partial electrodes 26 are respectively formed on another main surface 21b of each of the piezoelectric elements 21 such that the partial electrodes 26 extend over to the upper surfaces of the third dry film resists 24 (see FIG. 3(*a*)). As the partial electrodes 26, in a manner similar to the overall electrodes 25, for example, conductive metallic materials such as gold, copper, chromium and the like are used and are formed by using a sputtering apparatus, a vacuum evaporation (deposition) apparatus, and the like. On top of the third dry film resists 24 inclusive of each of the partial electrodes 26, a backing material 1 is formed. By the way, prior to the formation of the backing material 1, silver paste 7, for example, is arranged to be filled into the space defined by the apertures 22b, 23b, 24b for the wiring layer formation such that the wiring can be reinforced (see FIG. 3(*a*)).

In forming the backing material 1, first, in the same manner as the above, a fourth dry film resist 8 is adhered to the third dry film resist 24 inclusive of each of the partial electrodes 26 to form a single fourth aperture 81 so as to enclose the region in which each of the piezoelectric elements 21 is disposed in an array shape (see FIG. 3(*b*)). Then, the fourth aperture 81 is filled with a mixture, for example, of metallic powder and epoxy resin, and gets hardened to thereby form the backing material 1 (see FIG. 3(*c*)). The supporting body 5 is subsequently heated for releasing along an interface between the first dry film resist 22 and the release sheet 6 (see FIG. 3(*d*)). Then, after having mounted an acoustic matching part 3 on a lower surface of the first dry film resist 22, coupling is made from the backing material 1 side to the flexible wiring substrate 4. By the way, although not explained by particularly illustrating, as a result of connection of the flexible wiring substrate 4, the overall electrode 25, and each of the partial electrodes 26, an ultrasound probe AP of an array type is manufactured.

According to the above-mentioned embodiment, unlike the conventional art in which the piezoelectric elements are polished in the course of manufacturing the device, a plurality of piezoelectric elements 21 that have been polished in advance to predetermined thicknesses are prepared in advance, i.e., a plurality of piezoelectric elements 21 having uniform oscillatory frequency are prepared in advance. The first dry film resist 22 is exposed and developed so as to form the first apertures 22a arranged in an array shape. Each of the piezoelectric elements 21 is thus disposed relative to each of the first apertures 22a. Therefore, the product thus prepared will be such that each of the piezoelectric elements 21 to face from the first apertures 22 is disposed in an array shape at a predetermined distance from one another. Then, since each of the first through third dry film resists 22, 23, 24 is arranged to be adhered under conditions of heating, even if there is a minute clearance between, for example, the second aperture 23a and the piezoelectric element 21, part of each of the first through third dry film resists 22, 23, 24 gets molten to thereby fill the clearance. As a result, each of the piezoelectric elements 21 is firmly held by each of the first through third dry film resists 22, 23, 24 so that each of the piezoelectric elements 21 can be surely electrically insulated. In addition, since an arrangement has been employed in which each of the piezoelectric elements 21 is held by the respective first through third dry film resists 22, 23, 24, flexibility as the device will neither be impaired. In this manner, according to this invention, it becomes possible to manufacture, with a good yield, the products in which a plurality of piezoelectric elements 21 are disposed in an array shape at a predetermined distance from one another.

Description has so far been made of an embodiment of this invention, but changes can be made within a range in which the substance of this invention is not deviated, the substance being that the function elements (inclusive of the function part) are held by dry film resists to be laminated. Particularly, in case there are provided a plurality of function elements in which the function to make the effects more apparent varies with the thicknesses, the construction of the device and the method of manufacturing the device of this invention are suitable. In the above-mentioned embodiment, description has been made of an example in which the function element is made to be the piezoelectric element and is applied to an array type of ultrasound probe as a device. This invention shall, however, not be limited to the above.

Figure 4:
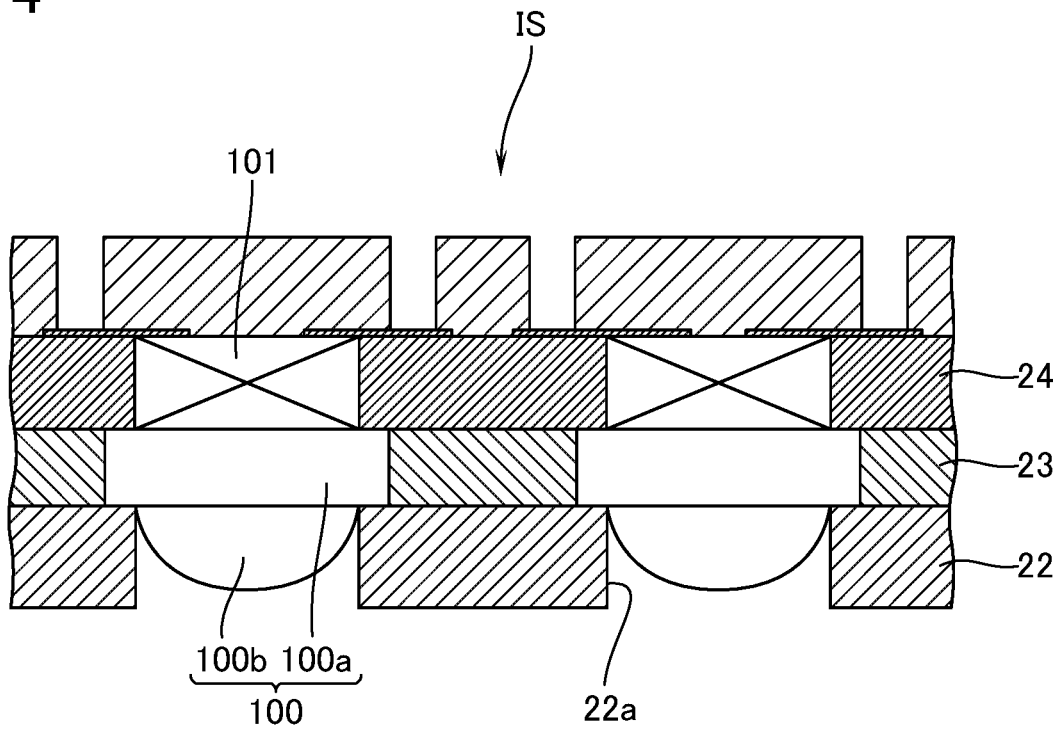
FIG. 4 is a sectional view, partly cut away, to explain a constitution of an image sensor as the device relating to another embodiment of this invention.

As shown in FIG. 4, in the case of an image sensor IS as a device having, as function parts, a micro lens 100 and light receiving element 101, the thickness of the micro lens 100 will give an effect on the sensitivity. Then, in the case of an image sensor IS relating to another embodiment of this invention, a plurality of micro lenses 100 having polished to a predetermined thickness are prepared, and in the same manufacturing processes as in the above-mentioned embodiment, by holding the micro lenses 100 by each of the first through third dry film resists 22, 23, 24, the image sensor IS is manufactured. In this case, as the second dry film resist 23, there was selected one having the thickness equivalent to the base end part 100a having a predetermined thickness of the micro lens 100. In a state of being held by each of the first through third dry film resists 22, 23, 24, the thickness of the first dry film resist 22 is set such that the lens part 100b is protruded into the first aperture 22a.

Figure 5:
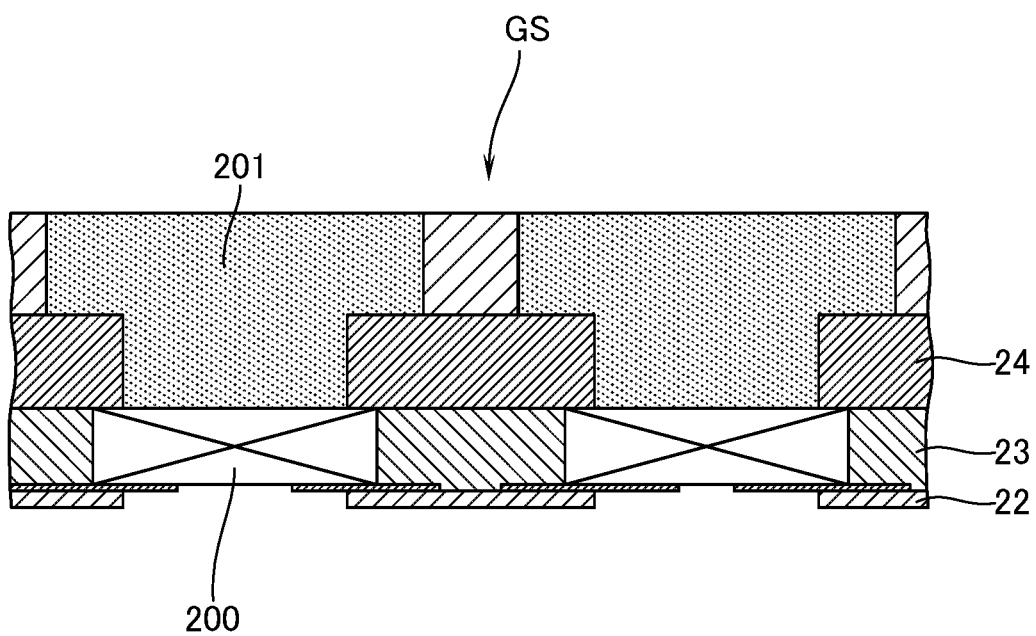
FIG. 5 is a sectional view, partly cut away, to explain a constitution of a gas sensor as the device relating to yet another embodiment of this invention.

Further, as shown in FIG. 5, in a gas sensor GS as a device provided with a crystal oscillator 200 as a function element, the thickness of the crystal oscillator 200 will affect the sensitivity. Therefore, in the gas sensor GS relating to another embodiment of this invention, a plurality of crystal oscillators 200 having been polished to a predetermined thickness are prepared, and in the same manufacturing processes as in the above-mentioned embodiment, by holding with each of the first through third dry film resists 22, 23, 24, the gas sensor GS is manufactured. By the way, in FIG. 5, reference numeral 201 denotes the gas to be measured.

EXPLANATION OF REFERENCE CHARACTERS

| AP | ultrasound probe (device) | | |
|---|---|---|---|
| 2 | ultrasound transmitter/receiver | | |
| 3 | piezoelectric element (function element) | | |
| 22 | first dry film resist | 22a | first aperture |
| 23 | second dry film resist | 23a | second aperture |
| 24 | third dry film resist | 23a | first aperture |
| 4 | backing material (carrier member) | | |
| 5 | support member | | |
| 6 | heat-peelable sheet (release sheet) | | |
| IM | image sensor (device) | | |
| 100 | micro lens (function part) | | |
| GS | gas sensor (device) | | |
| 200 | crystal oscillator (function element) | | |

The invention claimed is:

1. A device provided with a plurality of function elements of predetermined thicknesses, comprising:
   a first dry film resist having a plurality of first apertures formed in an array shape, and respectively supporting the function elements in close contact with a rim part of each of the first apertures in a state of partly exposing the function elements;
   a second dry film resist laminated on the first dry film resist, and also having second apertures respectively enclosing each of the function elements, the second dry film resist being of a thickness equivalent to that of each of the function elements; and
   a third dry film resist laminated on the second dry film resist, and also having third apertures, and respectively sandwiching each of the function elements with the first dry film resist in a state of partly exposing the function elements in close contact with a rim part of each of the third apertures.

2. The device according to claim 1, wherein the function elements are constituted as piezoelectric elements and wherein the device is constituted as an array type of ultrasound probe for measuring, by using a pulse-echo method, a diameter of blood vessel of a living body, the device further comprising:
   an overall electrode formed between the first dry film resist and one main surface of each of the respective piezoelectric elements;
   a partial electrode respectively formed on another main surface of each of the piezoelectric elements; and
   a backing material covering the partial electrode.

3. A method of manufacturing a device having a plurality of function elements of predetermined thicknesses, comprising the steps of:
   adhering, on one surface of a support member, a first dry film resist through a release sheet, and exposing and developing the first dry film resist, thereby forming a plurality of first apertures in an array shape;
   adhering, on a surface of the first dry film resist, a second dry film resist having a thickness equivalent to those of the function elements, and exposing and developing the second dry film resist, thereby forming, right above each of the first apertures, respective second apertures larger than the first apertures;
   disposing the function elements on an inside of the second apertures so as to be supported by rim parts of the first apertures;
   adhering, in a state of being heated, a third dry film resist on a surface of the second dry film resist, and exposing and developing the third dry film resist, thereby forming third apertures respectively so that the function elements are sandwiched together with the first dry resist film; and
   forming a carrier member on a surface of the third dry film resist, and releasing along an interface between the first dry film resist and the release sheet.

4. A method of manufacturing an array type of ultrasound probe for measuring, by using a pulse-echo method, a diameter of blood vessel of a living body, comprising the steps of:
   preparing a plurality of piezoelectric elements having equivalent thicknesses, and forming a first electrode film over an entire one main surface of each piezoelectric elements;
   adhering, through a release sheet, a first dry film resist on one surface of a support, and exposing and developing the first dry film resist, thereby forming a plurality of first apertures in an array shape;
   forming a second electrode film on the surface of the first dry film resist by patterning;
   adhering, on the surface of the first dry film resist on which the second electrode film has been formed, a second dry film resist having thicknesses equivalent to those of the piezoelectric elements, and exposing and developing the second dry film resist, thereby forming second apertures larger than the first apertures right above each of the first apertures;
   disposing, on an inside of the second apertures, piezoelectric elements from the main surface side on which the first electrode film has been formed, so as to be supported by rim parts of the first apertures to thereby make an overall electrode in which the first electrode film and the second electrode film are connected to each other;
   adhering, in a state of being heated, a third dry film resist on a surface of the second dry film resist inclusive of another main surface of the piezoelectric elements, and exposing and developing the third dry film resist, thereby forming third apertures so as to sandwich the piezoelectric elements together with the first apertures;

forming partial electrodes respectively on another main surface; and forming a backing material serving as a carrier member to cover the third dry film resist and the partial electrodes, and releasing along an interface between the first dry film resist and the release sheet.

\* \* \* \* \*